United States Patent
Piskun et al.

(10) Patent No.: US 9,161,746 B2
(45) Date of Patent: Oct. 20, 2015

(54) SUBSTAINTIALLY RIGID AND STABLE ENDOLUMINAL SURGICAL SUITE FOR TREATING A GASTROINTESTINAL LESION

(71) Applicants: Gregory Piskun, Morganville, NJ (US); Dan Rottenberg, Haifa (IL); Boaz Manash, Givat-Ada (IL); Dima Pinhasov, Naharia (IL)

(72) Inventors: Gregory Piskun, Morganville, NJ (US); Dan Rottenberg, Haifa (IL); Boaz Manash, Givat-Ada (IL); Dima Pinhasov, Naharia (IL)

(73) Assignee: Macroplata, Inc., Morganville, NJ (US)

( * ) Notice: Subject to any disclaimer, the term of this patent is extended or adjusted under 35 U.S.C. 154(b) by 180 days.

(21) Appl. No.: 13/726,147

(22) Filed: Dec. 23, 2012

(65) Prior Publication Data

US 2013/0144118 A1    Jun. 6, 2013

Related U.S. Application Data

(63) Continuation of application No. 12/970,604, filed on Dec. 16, 2010, now Pat. No. 8,506,479.

(60) Provisional application No. 61/287,077, filed on Dec. 16, 2009.

(51) Int. Cl.
*A61B 1/32* (2006.01)
*A61B 17/02* (2006.01)
(Continued)

(52) U.S. Cl.
CPC ........... *A61B 17/0218* (2013.01); *A61B 1/0051* (2013.01); *A61B 1/00082* (2013.01); *A61B 1/00085* (2013.01); *A61B 1/00087* (2013.01); *A61B 1/00154* (2013.01); *A61B 1/018* (2013.01); *A61B 1/31* (2013.01); *A61B 1/32* (2013.01); *A61B 17/00234* (2013.01); *A61B 2017/00557* (2013.01); *A61B 2017/0225* (2013.01); *A61B 2017/345* (2013.01); *A61M 25/1011* (2013.01); *A61M 2025/1052* (2013.01)

(58) Field of Classification Search
CPC ....................................................... A61B 1/32
See application file for complete search history.

(56) References Cited

U.S. PATENT DOCUMENTS

| 457,787 | A | 8/1891 | Leisenring |
| 4,083,369 | A | 4/1978 | Sinnreich |

(Continued)

FOREIGN PATENT DOCUMENTS

| GB | 2365340 | 2/2002 |
| JP | 2533732 | 4/1997 |

(Continued)

OTHER PUBLICATIONS

International Preliminary Report on Patentability dated Jun. 28, 2012 for International Application No. PCT/US2010/060802.

(Continued)

*Primary Examiner* — Nicholas Woodall

(57) ABSTRACT

Exemplary embodiments of devices and method for affecting at least one anatomical tissue can be provided. A configuration can be provided that includes a structure which is expandable (i) having and/or (ii) forming at least one opening or a working space through which the anatomical tissue(s) is placed in the structure. For example, the structure, prior to being expanding, can have at least one partially rigid portion. In addition, or as an alternative, upon a partial or complete expansion thereof, the structure can be controllable to have a plurality of shapes. Further, the structure can be controllable to provide the working space with multiple shapes and/or multiple sizes.

21 Claims, 15 Drawing Sheets

(51) Int. Cl.
*A61B 1/00* (2006.01)
*A61B 1/018* (2006.01)
*A61B 17/00* (2006.01)
*A61B 1/005* (2006.01)
*A61B 1/31* (2006.01)
*A61M 25/10* (2013.01)
*A61B 17/34* (2006.01)

(56) References Cited

U.S. PATENT DOCUMENTS

| | | |
|---|---|---|
| 4,295,464 A | 10/1981 | Shihata |
| 5,087,265 A | 2/1992 | Summers |
| 5,197,971 A | 3/1993 | Bonutti |
| 5,386,817 A | 2/1995 | Jones |
| 5,411,508 A | 5/1995 | Bessler et al. |
| 5,423,830 A | 6/1995 | Schneebaum et al. |
| 5,655,698 A | 8/1997 | Yoon |
| 5,776,097 A | 7/1998 | Massoud |
| 5,947,983 A | 9/1999 | Solar et al. |
| 5,954,731 A | 9/1999 | Yoon |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,214,024 B1 | 4/2001 | Houser |
| 6,264,086 B1 | 7/2001 | McGuckin et al. |
| 6,302,311 B1 | 10/2001 | Adams et al. |
| 6,343,731 B1 | 2/2002 | Adams et al. |
| 6,428,473 B1 | 8/2002 | Leonard et al. |
| 6,494,881 B1 | 12/2002 | Bales et al. |
| 6,616,603 B1 | 9/2003 | Fontana |
| 6,695,198 B2 | 2/2004 | Adams et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams et al. |
| 7,059,331 B2 | 6/2006 | Adams et al. |
| 7,169,115 B2 | 1/2007 | Nobis et al. |
| 7,445,598 B2 | 11/2008 | Orban |
| 8,517,933 B2 | 8/2013 | Mohr |
| 8,608,652 B2 * | 12/2013 | Voegele et al. ............... 600/207 |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0074015 A1 | 4/2003 | Nakao |
| 2003/0135230 A1 * | 7/2003 | Massey et al. ............... 606/190 |
| 2003/0225433 A1 | 12/2003 | Nakao |
| 2004/0158263 A1 | 8/2004 | McAlister et al. |
| 2004/0204725 A1 | 10/2004 | Bayer |
| 2005/0240147 A1 | 10/2005 | Makower et al. |
| 2005/0251177 A1 | 11/2005 | Saadat et al. |
| 2006/0074277 A1 | 4/2006 | Yoshida |
| 2006/0189845 A1 | 8/2006 | Maahs et al. |
| 2006/0191975 A1 | 8/2006 | Adams et al. |
| 2006/0264706 A1 | 11/2006 | Piskun |
| 2007/0255207 A1 | 11/2007 | Hangai et al. |
| 2007/0293724 A1 | 12/2007 | Saadat et al. |
| 2008/0045842 A1 | 2/2008 | Furnish |
| 2008/0132835 A1 | 6/2008 | Nagamatsu et al. |
| 2008/0269559 A1 | 10/2008 | Miyamoto et al. |
| 2008/0275300 A1 | 11/2008 | Rothe et al. |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2010/0010296 A1 | 1/2010 | Piskun et al. |
| 2010/0106240 A1 | 4/2010 | Duggal et al. |
| 2011/0172491 A1 | 7/2011 | Piskun et al. |
| 2012/0109178 A1 | 5/2012 | Edwards et al. |

FOREIGN PATENT DOCUMENTS

| | | |
|---|---|---|
| JP | 2000-325303 | 11/2000 |
| WO | WO 9635469 | 11/1996 |
| WO | WO2009-059296 | 5/2009 |
| WO | WO2009/117696 | 9/2009 |
| WO | WO 2011/084616 | 7/2011 |

OTHER PUBLICATIONS

European Search Report dated Jun. 1, 2014 for International Application No. PCT/US2014/040429.
European Search Report dated May 3, 2011 for European Patent Application No. 06789411.3.
Written Opinion dated Jun. 20, 2007 for International Application No. PCT/US06/30464.
Chinese Office Action dated May 12, 2009 for Chinese Application No. 200680028706.2.

* cited by examiner

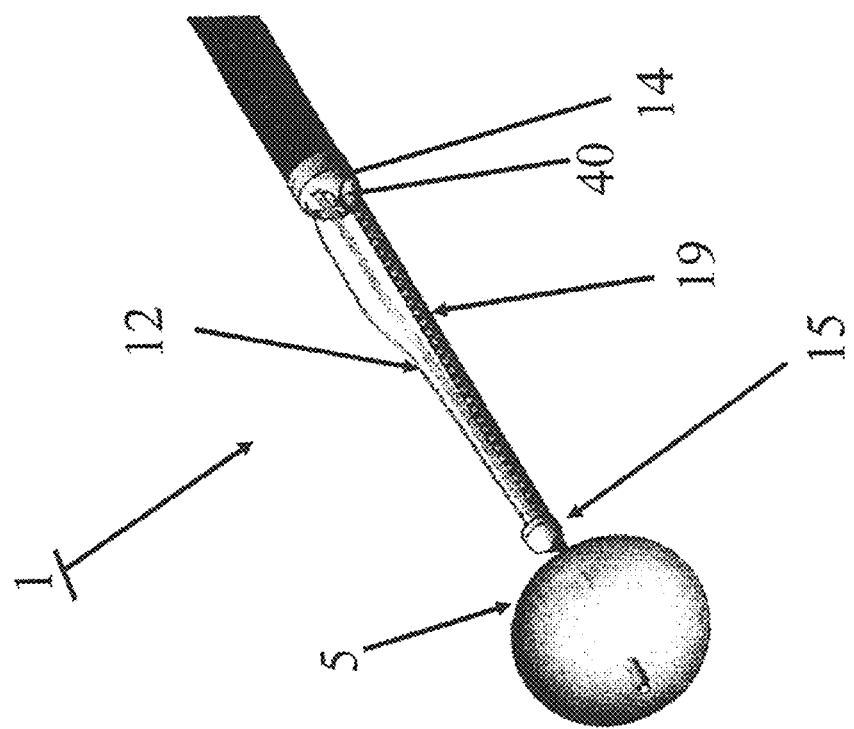
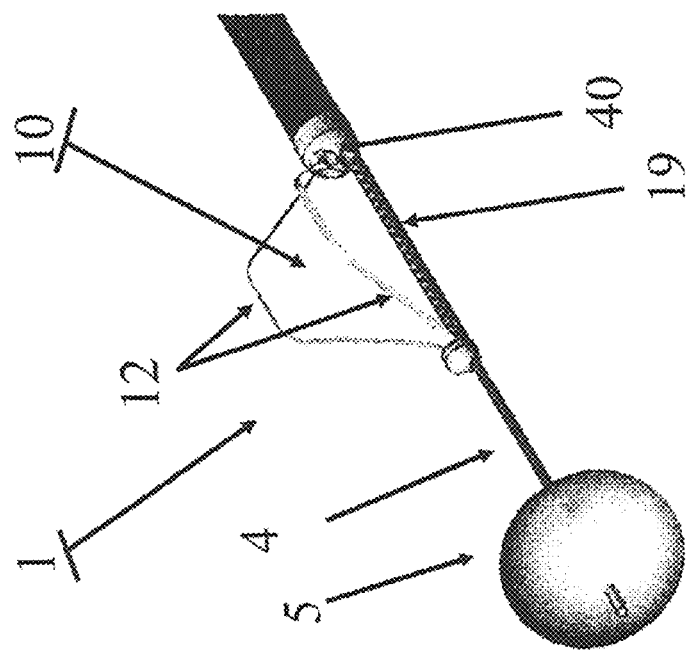
Fig. 2
Fig. 2A

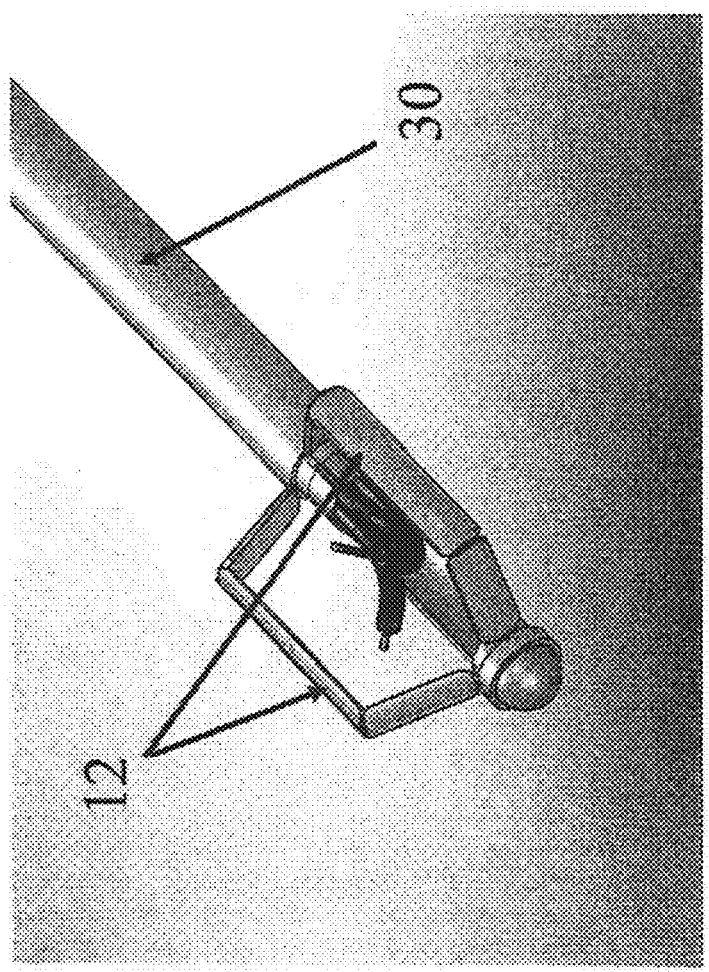

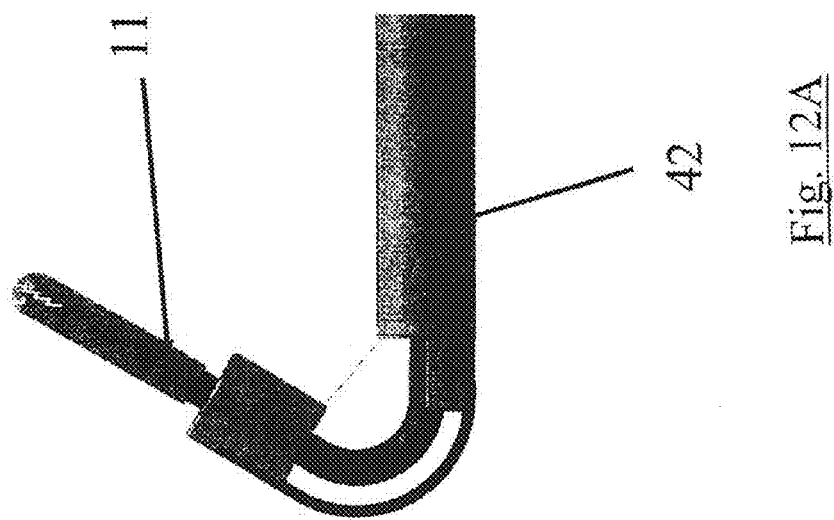
Fig. 12A
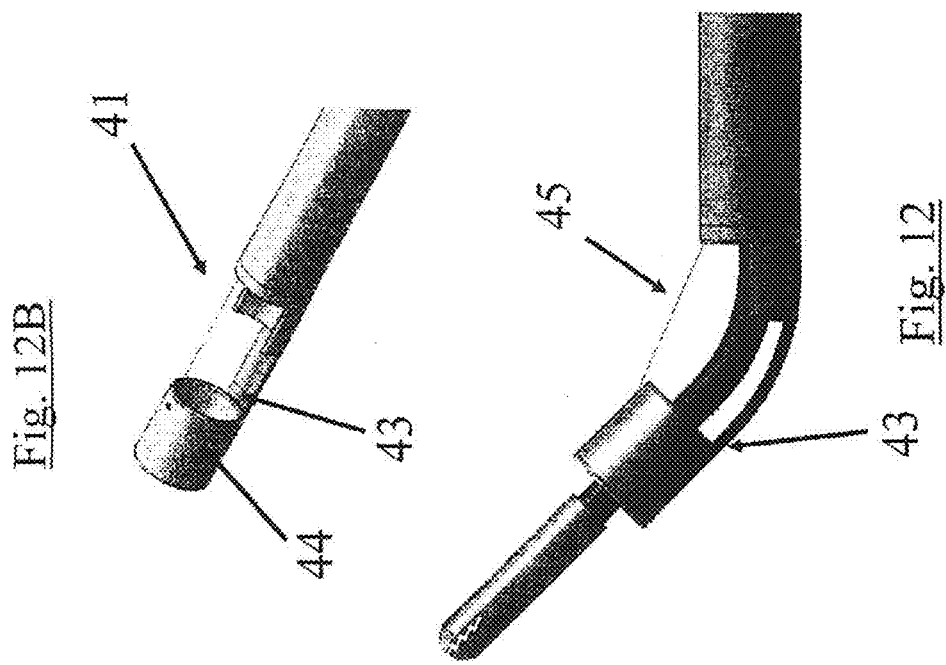
Fig. 12B
Fig. 12

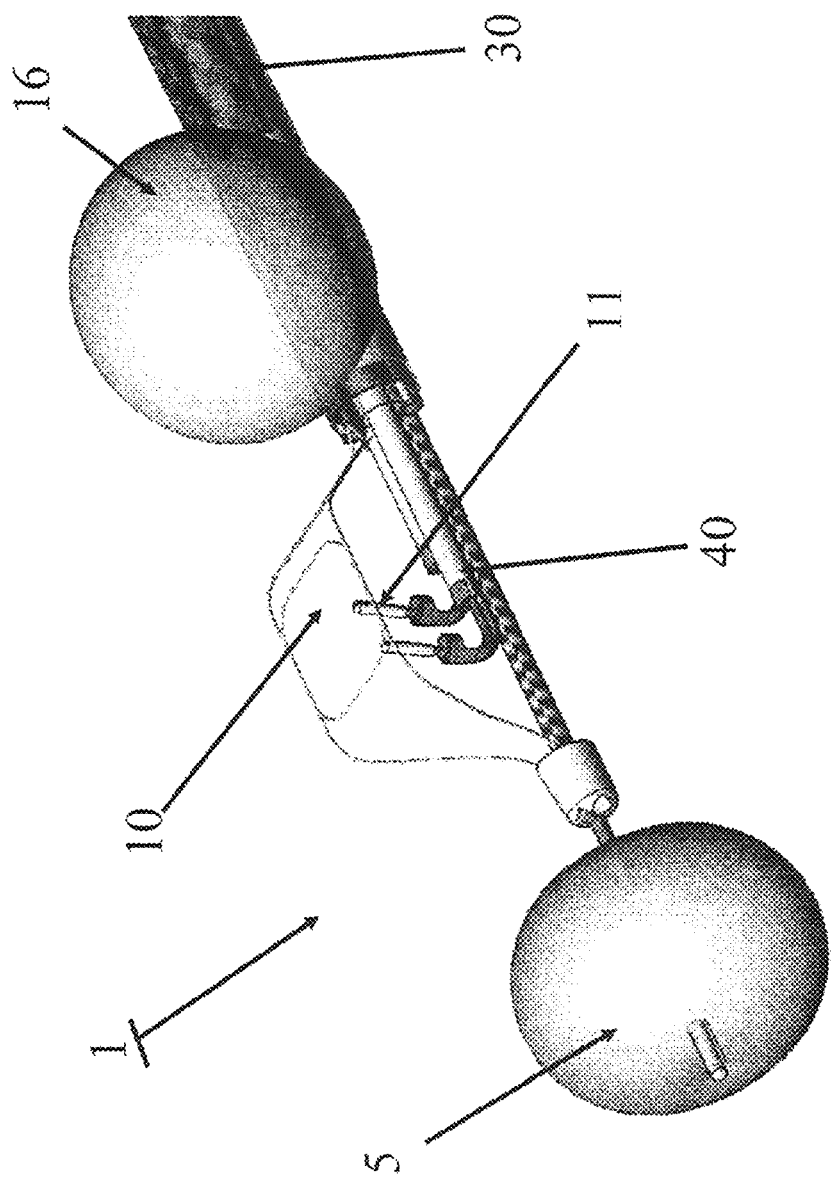

SUBSTAINTIALLY RIGID AND STABLE ENDOLUMINAL SURGICAL SUITE FOR TREATING A GASTROINTESTINAL LESION

CROSS REFERENCE TO RELATED APPLICATION

This application is a continuation of U.S. patent application Ser. No. 12/970,604, filed Dec. 16, 2010, which claims priority from U.S. Provisional Patent Application No. 61/287,077, filed Dec. 16, 2009. The contents of these applications are incorporated by reference in their entirety herein.

FIELD OF THE DISCLOSURE

Exemplary embodiments of the present disclosure relate to arrangements and methods for effecting an endoluminal anatomical structure, and more particularly to arrangements and methods for treatment of gastrointestinal lesions that currently require open abdominal surgery. The exemplary embodiment of at least one of the arrangements can provide an endoluminal colon chamber and a variety of maneuverable operating tools inside that chamber. For example, the exemplary embodiment of such arrangement can function as a miniature operating room inside the colon.

BACKGROUND INFORMATION

Current endoscopic technologies may not facilitate treating colon perforations, large polyps and tumors, and a significant colon bleeding effectively and safely. A gastrointestinal bleeding is a common and potentially life-threatening medical condition, which can complicate any polypectomy (polyp removal), and excision of colonic tumors. A colon perforation can occur when excessive mechanical force or excessive energy is inadvertently applied to a colonic wall. A colon perforation is a life-threatening condition and currently requires major emergency surgery to close the colon perforation and preclude fecal contamination of an abdominal cavity and resulting sepsis.

Consequently, many patients who develop large polyps, colon perforation, colon bleeding and other significant colon pathology currently have to undergo a major surgery and endure a significant operative trauma and, typically, painful and prolong recovery. Currently there are no effective and safe devices and methods for replacing major abdominal surgery in case of colon perforation or when large wide-based polyps need to be removed.

Thus, there may be a need to address at least some of the deficiencies described herein above.

U.S. Provisional Patent Application Ser. No. 61/247,605 filed on Oct. 1, 2009 and entitled "Detachable Balloon Catheter" describes exemplary embodiments of device and method for treatment of a gastrointestinal perforation and/or a gastrointestinal bleeding. The exemplary device can include a balloon catheter that can control bleeding by pressing on a bleeding area or/and prevents the gastrointestinal contents trespassing outside a gastrointestinal lumen into a body cavity by blocking an opening in the luminal wall or blocking the colon distal to the perforation. Such exemplary device can be inserted using an endoscope, and can allow a partial or complete withdrawal of an endoscope, while leaving the balloon at the target area. More specifically, the exemplary device and method can facilitate ceasing a colonic bleeding and blocking a colon perforation.

The Minos Megachannel is a large bore flexible reinforced tube, which is designed to be inserted over the standard colonoscope. After the colonoscope is removed, the tube can be used as a passage for insertion of different instruments into the colon.

Further, conventional endoscopes generally have one to two working channels, which likely do not have independent movements from the main body of the endoscope. As a result, when conventional flexible endoscopic instruments are inserted via such channels into the intestinal lumen, an operator can only manipulate these instruments axially (e.g., forward and backward movements), and possibly somewhat rotationally. In addition, since the conventional instruments can only be advanced from the tip of the endoscope towards the target lesion axially and in front of the endoscopic image, the conventional instruments have only limited functionality.

Accordingly, there may be a need to address at least some of the deficiencies described herein above.

SUMMARY OF EXEMPLARY EMBODIMENTS OF THE PRESENT DISCLOSURE

Exemplary embodiments of the present disclosure can address most if not all of the above-described needs by providing device and method for a treatment of, e.g., a gastrointestinal perforation, bleeding, removal of large polyps, and/or other significant endoluminal pathology, for example, colonic pathology.

According to one exemplary embodiment of the present disclosure, the device can function as a miniature operating room inside the lumen, for example, colon, and providing an operator with advanced endoluminal functionalities replicating capabilities of a surgical suite. The exemplary device of the present disclosure can provide such miniature endoluminal operating room, chamber or at least partial enclosure, and the ability to utilize a variety of articulating surgical instruments, which can operate within, at or around the chamber.

According to one exemplary embodiment of the present disclosure, the exemplary arrangement/device can be introduced after a standard diagnostic colonoscopy is performed. An exemplary balloon guide catheter, as described in U.S. Provisional Patent Application Ser. No. 61/247,605, or a large endoluminal channel such as a Minos Megachannel manufactured by, e.g., Minos Inc., can be used to facilitate the insertion of the exemplary device according to the present disclosure.

In another exemplary embodiment of the present disclosure, the arrangement/device can contain a plurality (e.g., three) primary sections, e.g., a handle, a multi-lumenal tube, and an expandable chamber.

It is possible to utilize endoluminal channels and associated articulating endoluminal instruments with the exemplary embodiments of the arrangement/device. To that end, the exemplary arrangement/device can include a multi-lumen tube. The multi-lumen tube can include lumens for at least two special tools or tool-channels, or three or more special tools and/or tools-channels. In addition, the multi-lumen tube can include other channels, which can be used for, as an example, air, water, vacuum delivery, etc. The exemplary arrangement/device can also include channel for scope and illumination; and lumens for a chamber activation and lumen for a balloon guide catheter as indicated herein.

According to still another exemplary embodiment of the present disclosure, the arrangement/device may also contain a chamber located distally, which can be expanded to different sizes within the colon, thus producing a relatively large working space near the targeted luminal lesion. The exemplary arrangement/device can be structured to manipulate the tools and/or tool-channels in such a way that distal ends of one or more of such tools and/or channels can operate within or at the chamber, and approach the lesion from multiple or even all directions, and using numerous angles. In addition, at least one tool-channel can accommodate a large diameter tool, for example, a special endoscopic stapler.

In a further exemplary embodiment of the present disclosure, the arrangement/device can further contain a control handle, e.g., at or about its proximal end. The handle can be provided in a similar way and/or shape as handles of other endoscopes', while including further more ports, such as, e.g., tool-channels ports, a balloon guide catheter port, a special lever to control the opening and closing of the device chamber, etc.

According to a still further exemplary embodiment of the present disclosure, the arrangement/device can include and/or utilize particular tools or tool-channels. For example, the distal ends of the particular tools and/or tool-channels can be operated in all directions and within all degrees of freedom using the actuating mechanisms, which can be controlled at or about the proximal ends of the device. The exemplary instruments/tools (e.g., grasper(s), scissor(s), dissector(s), others), which can be inserted in the special tools or tool-channels, may be manipulated (e.g., rotated, moved axially forward and backward, bent at the distal end at any desired angles) by manipulating the tool-channels.

In a further exemplary embodiment of the present disclosure, the arrangement/device can facilitate a lateral and/or multi-directional movements of the instruments/tools, in addition to the axial and rotational movements thereof. Since the exemplary tool-channels can be manipulated independently from the main endoscope and other tool-channels, the instruments/tools can approach the lesion from the different and possibly limitless directions. For example, when the endoscopic instruments/tools approach the lesion from the sides in relation to the main longitudinal axis and, hence, without blocking the endoscopic image, a so-called and well-known in laparoscopy "tri-angulation" can be achieved. The tri-angulation can be a preferable technique for achieving the endoscopic arrangement's/device's improved functionality and safety. Such exemplary methodology can mimic the functionality of well-established surgical operating room environments. The exemplary tool-channels can be advanced in the lumen from the working ports of the multi-lumen tube and/or be at least partially pre-fixed to the element(s) of the associated expandable chamber. The exemplary tool-channels can also be advanced directly into the body lumen (e.g., an intestinal lumen), into the chamber space, and/or initially advanced along the element(s) of the chamber and then further into the body lumen or into the chamber space.

As an alternative according to yet another exemplary embodiment of the present disclosure, the arrangement/device, alternatively to the tool-channels or in combination with the tool-channels, can use conventional and/or articulating instruments/tools with at least two degree of freedom.

In addition, according to a further exemplary embodiment of the present disclosure, a method can be provided for using the exemplary arrangement/device in the body lumen (e.g., colon). For example, using such exemplary method, it is possible to perform a standard colonoscopy and identify a lesion that may not be treated using standard endoscopy and techniques. A balloon guide catheter can be inserted, the balloon inflated and the standard colonoscope (the balloon catheter and inflated balloon are left in place) removed. The balloon guide catheter can be used as a guide-wire to facilitate the insertion of the exemplary arrangement/device. The exemplary arrangement/device can be inserted over the balloon guide catheter, e.g., until the chamber is in the proximity to the lesion. The chamber can be deployed and adjusted to certain dimensions. It is possible to readjust the chamber during the procedure, as needed. Further, an operative area can be cleaned with a provided suction catheter. Further, a proximal balloon, a distal balloon or both proximal and distal balloons can be inflated for the treatment area isolation. Tool-channels can be inserted, followed by or in conjunction with an insertion of the instruments/tools into the tool-channels. It is also possible to manipulate the tool-channels to optimize and facilitate the instruments'/tools' approach to the lesion. Further, a procedure can be performed, for example, closing a colonic perforation, removing a large colon polyp or tumor, stopping a bleeding, closing diverticuli, removing an appendix, treating other body luminal lesions.

Further, exemplary embodiments of devices and method for affecting at least one anatomical tissue can be provided. A configuration can be provided that includes a structure which is expandable (i) having and/or (ii) forming at least one opening or a working space through which the anatomical tissue(s) is placed in the structure. For example, the structure, prior to being expanding, can have at least one partially rigid portion. In addition, or as an alternative, upon a partial or complete expansion thereof, the structure can be controllable to have a plurality of shapes. Further, the structure can be controllable to provide the working space with multiple shapes and/or multiple sizes.

According to yet another exemplary embodiment of the present disclosure. prior to the structure being expanded, the structure can have at least one partially rigid portion that is expandable to form a non-cylindrically-shaped working area which can be asymmetrical. Further, an endoscopic arrangement can be included that is structured to be provided in the working area, and that can include a further configuration that facilitates an articulation of a tip portion of the endoscopic arrangement within the working area. The further configuration can include a mechanical bending arm which can facilitate the tip portion to be moved within the working area so as to facilitate a visualization of at least one object in the working area. An arrangement can also be provided which is coupled to the structure, and which can provide (i) at least one lumen and/or (ii) at least one instrument there through to reach the working area. For example, a distance between a tip of the arrangement and a distal portion of the structure that is farthest away from the arrangement can be controllable to adjust a shape and/or a size of the working area.

In still another exemplary embodiment of the present disclosure, upon a complete or partial expansion of the structure, the structure can be controllable to have a plurality of shapes. In addition, the structure can be controllable to provide the working space with multiple shapes and/or multiple sizes. The structure can have an expanded portion and an unexpanded portion, and form an axes of extension of the device, a first distance to a highest point of the expanded portion can be different than a distance to an non-expanded portion. For example, the first distance can be greater than the second distance. The structure can be controllable to adjust the first distance, while maintaining the second distance approximately the same. Further, in an non-expanded state, the configuration can be controllable to provide an articulation thereof in a plurality of directions.

According to a further exemplary embodiment of the present disclosure, a first arrangement can be provided at a distance from the configuration and the anatomical structure(s). In addition, a second arrangement can be provided between the first arrangement and the configuration, and can have at least one lumen that is connected to the first arrangement. Further, a third arrangement can be provided which may be structured to move through the lumen at or near the anatomical structure(s), and which can be configured to be provided in the structure. The lumen(s) can comprise a multi-channel tube, and the structure can be structured to be movable through the multi-channel tube and rigidly connected thereto so as to limit or reduce a movement of the structure with respect to the multi-channel tube. At least one movable camera and an illumination arrangement can be provided within or near the configuration, and movable through the multi-channel tube. At least one movable vacuum catheter and/or irrigation catheter can be provided within or near the structure, and movable through the multi-channel tube.

In one exemplary embodiment, the lumen(s) can comprise a tube channel and/or a tool channel, which is/are movable therein. The tool channel can be axially movable, rotatable, and/or bendable, and can include at least one wire which is configured to bend the tool channel. A distal end of the tool channel can be configured to reach any point inside or near the structure. The tool channel can include at least one wire which can be usable to bend the tube or the tool channel at least in one direction and in at least at one angle which is between 0 and 180 degrees. For example, a distance between the working channel and the structure can be controllable by moving at least one wire in the working channel toward and/or away from the structure. An endoscope can be provided within or near the configuration, and movable through the multi-channel tube to reach the working space. The endoscope can include an image sensor provided on a flexible shaft to visualize at least one portion of the tissue(s).

According to yet a further exemplary embodiment of the present disclosure, the structure can have at least one flexible strip or at least one wire and/or two or more flexible strips or wires. At least one of the strips or wires can have a pre-formed shape to provide the desired geometry of the working space. In addition, at least one balloon can be provided or two or more balloons. At least one of the balloons can be an asymmetric shape and/or a symmetric shape. The balloon(s) can be positioned proximal to the structure. According to one exemplary variant, a first balloon and a second balloon can be provided, where the first balloon is provided distally in relation to the structure, and the second balloon is provided proximally in relation to the structure. The structure can be composed of wires and/or a mesh. Such wires/mesh, prior to being expanded, can have (i) at least one partially rigid portion, (ii) upon a partial or complete expansion thereof, can be controllable to have a plurality of shapes, and/or (iii) can be controllable to provide the working space multiple shapes and/or multiple sizes.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present disclosure, in which:

FIG. 2 is a perspective view of an exemplary embodiment of the arrangement/device according to the present disclosure comprising which includes a nitinol strips chamber in an position;

FIG. 2A is a perspective illustration of the arrangement/device of FIG. 2 with the chamber formed by flexible strips in an open position;

FIG. 3 is a perspective view of another exemplary embodiment of the arrangement/device according to the present disclosure which includes the chamber made from two metal strips;

FIG. 9A is a left side perspective view the exemplary arrangement/device of FIG. 9;

FIGS. 12, 12A and 12B are different illustrations of a preferred embodiment of still another exemplary of the arrangement/device according to the present disclosure which includes a tool-channel elevator with FIG. 12 showing the device in a first bent position, FIG. 12A showing the device in a second bent position, and FIG. 12B showing the device in a non-bent position; and FIG. 13 a perspective view of yet another exemplary of another exemplary embodiment of the arrangement/device according to the present disclosure which includes the tool-channels inside the chamber thereof.

Figures 1, 1A:
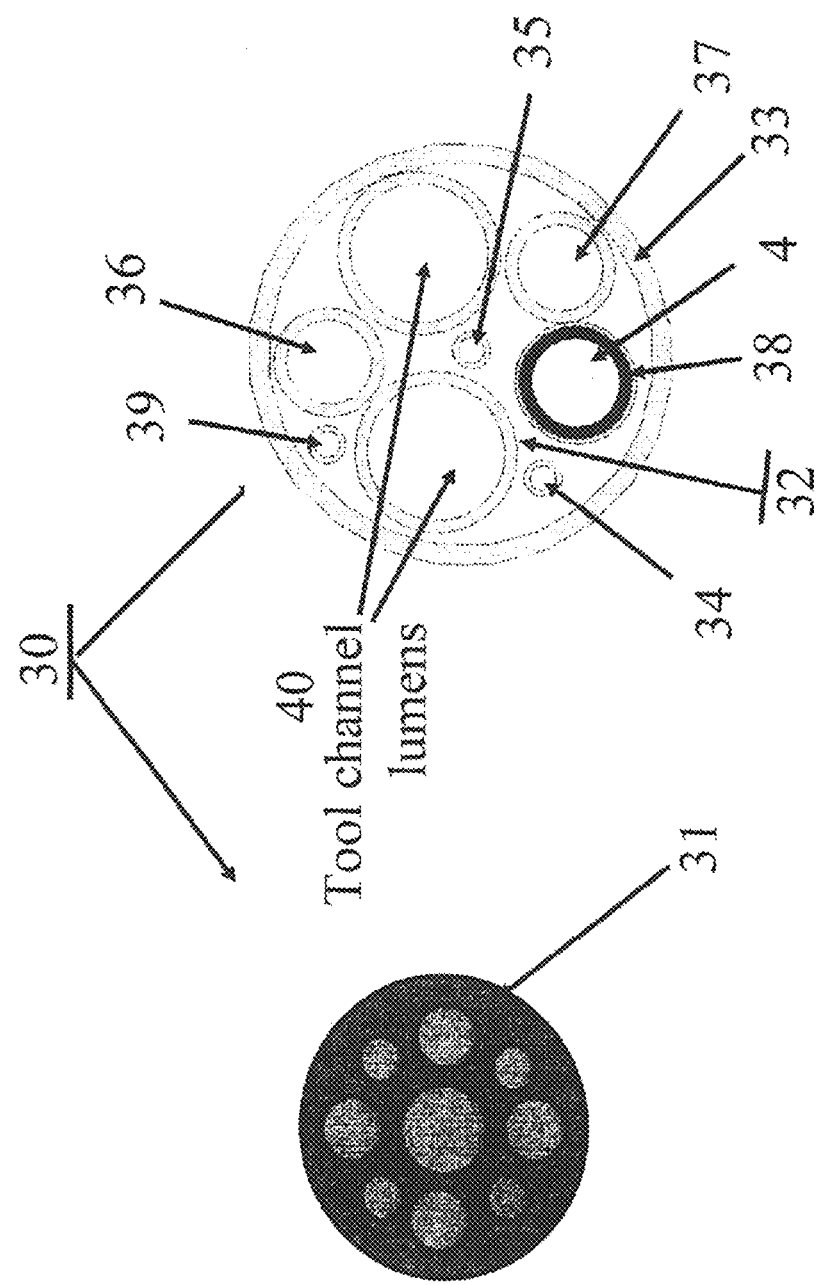
FIGS. 1 and 1A, are schematic cross-sectional illustrations of an exemplary embodiment of an arrangement/device comprising a multi-lumen extrusion tube, and multiple tubes inside one large tube in accordance with the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

According to one exemplary embodiment of the present disclosure, a device, an arrangement and a method can be provided for treatment of, e.g., conditions associated with body lumen(s) or/and cavities, for example, gastro-intestinal conditions, including but not limited to a gastrointestinal perforation, bleeding, large polyps or/and tumors, diverticuli, appendix, and others.

The exemplary embodiments of the arrangement/device according to the present disclosure can provide various functions, which may be the same and/or similar to the surgical functions provided in the surgical operating room, therefore, thus representing a miniature operating room within a lumen (e.g., of a body), such as, e.g., colon and allowing to replace a major surgery, e.g., an open abdominal surgery.

For example, as shown in FIGS. 2 and 2A, the exemplary embodiment of the arrangement/device 1 according to the present disclosure can provide an endoluminal chamber which can also be at least partial enclosure, such as, e.g., an endoluminal colon or an intra-colon chamber/enclosure, and include various maneuverable operating instruments and/or tools 11 within the chamber 10. The exemplary arrangement/device 1 can be inserted after one or more relevant lesions is/are identified, e.g., during standard colonoscopy. A particular balloon guide catheter 4, e.g., such as described in U.S. Provisional Patent Application Ser. No. 61/247,605 filed on Oct. 1, 2009, or Mega-channel such as Minos Inc. Mega-channel, can be used to facilitate an insertion of the exemplary arrangement/device 1.

Figure 8:
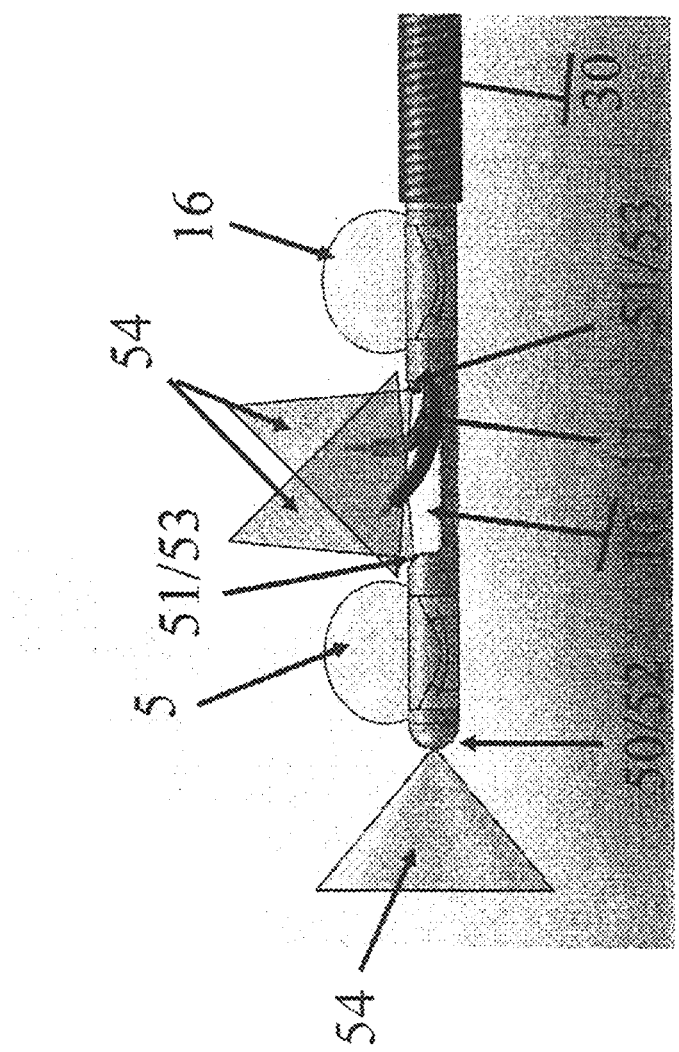
FIG. 8 is a side view of another exemplary of yet a further exemplary embodiment of the arrangement/device according to the present disclosure which includes the chamber with cameras.
Figure 9:
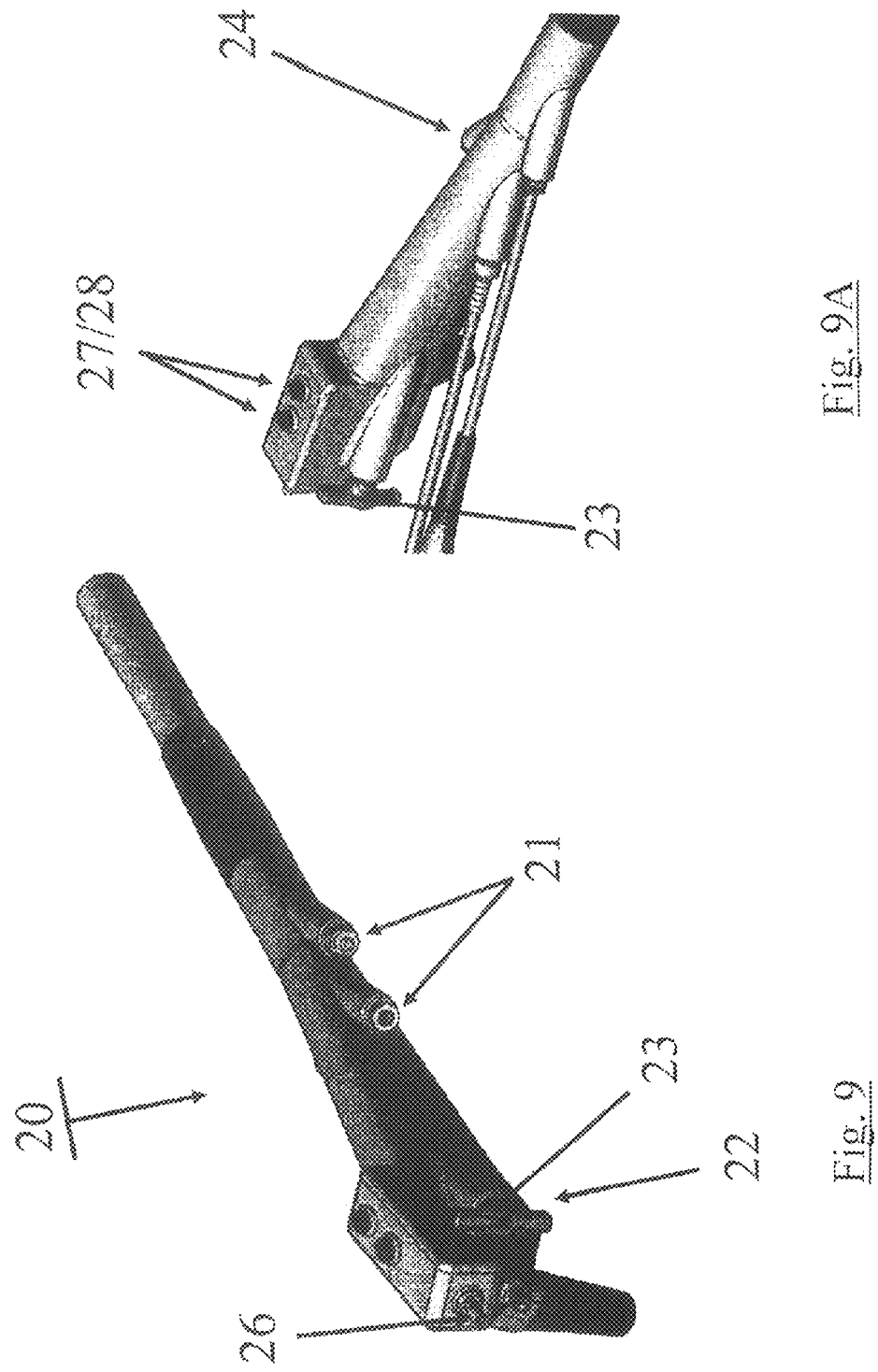
FIG. 9 is a right side perspective view of a further exemplary embodiment of the arrangement/device according to the present disclosure which includes a particular handle.

According to certain exemplary embodiments of the present disclosure, the arrangement/device 1 can be a particularly-designed endoscope, such as, e.g., a colonoscope. As shown in FIGS. 9 and 9A, according to certain exemplary embodiments, the arrangement/device 1 can include, e.g., an exemplary handle 20 (see FIGS. 9 and 9A), an exemplary multi-lumen tube 30 (see FIGS. 1, 1A, 3, 7, 8 and 13), and an exemplary expandable chamber 10 (see FIGS. 5, 7, 10 and 13). In addition, the arrangement/device 1 can include standard and particular exemplary instruments/tools 11 (see FIGS. 8, 12 and 13) and/or exemplary tool channels (see FIG. 13).

As indicated herein above, the exemplary arrangement/device 1 can include the multi-lumen tube 30. Such exemplary multi-lumen tube 30 can be made from a single extrusion polymer tube 31 having multiple lumens {see FIG. 1}, and/or made in a standard endoscopic equipment configuration using a collection of single or multi-lumen tubes 32 of different sizes that are enclosed by a single, large, flexible tube 33 (see FIG. 1A). External and internal tubes can be simple polymer tubes and/or reinforced tubes or braided tubes, as known in the art. The external tube 33 can have a diameter that is large enough to contain all inner tubes 32 provided for the exemplary arrangement/device 1. The exemplary multi-lumen tube 30 can include at least one lumen, and, e.g., possibly 2 to 4 or more lumens for 2 to 4 or more exemplary instruments/tools 11 and/or tool-channels 40, and possibly additional lumens, for example, for a air insufflation 34, water irrigation 35, vacuum 36, lumen for wiring and/or fibers for cameras and illumination 37, lumen for a balloon guide catheter 4, lumen for chamber expansion control 38, and/or lumen for proximal balloon inflation 39, as shown in the exemplary embodiment of FIG. 1A.

For example, according to particular exemplary embodiments of the present disclosure, the arrangement/device 1 can contain a distal chamber 10 that can be expanded to different sizes inside the colon, thus likely creating relatively large or sufficient working space near the lesion to be treated. The exemplary chamber 10 can provide a space for manipulations of multiple tools and/or tool-channels in such a way that several tools can approach the lesion from all sides and directions, as shown in, e.g., FIGS. 3, 7, 8 and 13. The exemplary multi-lumen tube 30, e.g., having a diameter between 10 mm to 40 mm, can accommodate at least one tool-channel, which can in turn accommodate, e.g., a non-standard instrument, for example, an endoscopic stapler, both having a sufficient size for a particular purposes thereof.

Figure 2B:
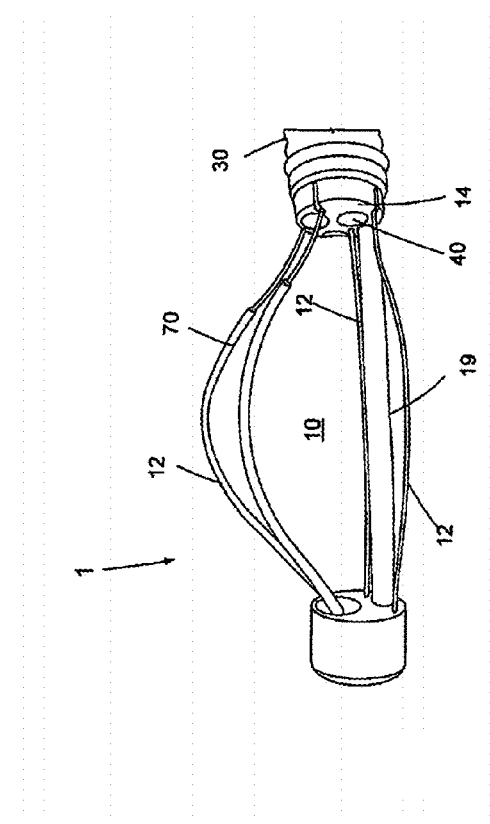
FIG. 2B is a side view of the arrangement/device of FIG. 2 with the chamber formed by flexible strips in another position.
Figure 2C:
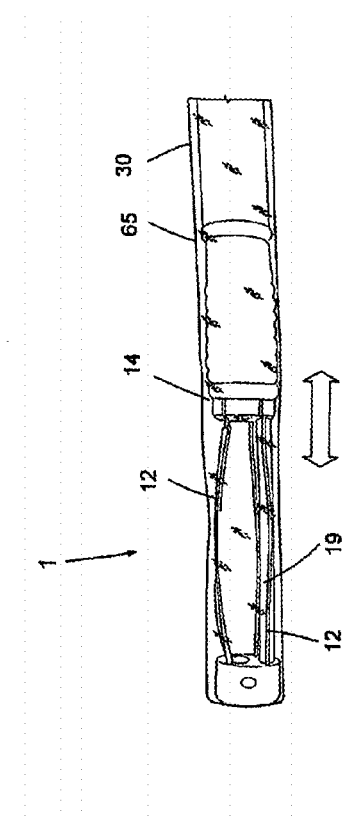
FIG. 2C is a side view of the arrangement/device of FIG. 2 with an overtube covering the chamber that is in the closed position according to an exemplary embodiment of the present disclosure.
Figure 2D:
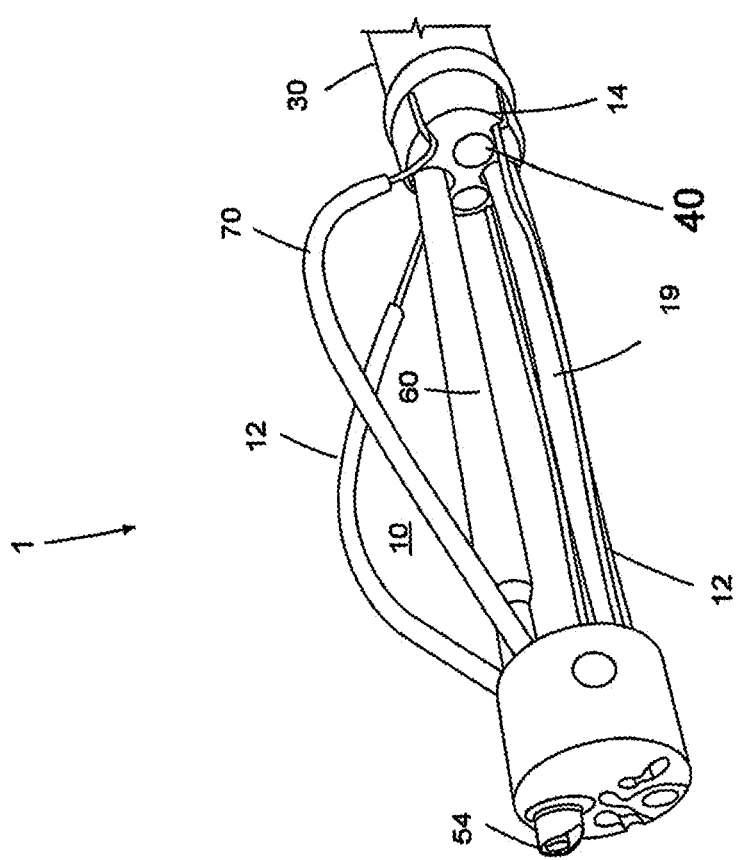
FIG. 2D is a side view illustration of the arrangement/device of FIG. 2 with a scope that is provided in one of the working channels and facilitating a field of view therefor according to another exemplary embodiment of the present disclosure.

According to one exemplary embodiment of the present disclosure, the exemplary chamber 10 can be constructed from at least one, and possibly two or more flexible metal strips, fibers or wires 12, which can be made from a flexible material, such as, e.g., Nitinol, as shown in FIGS. 2, 2D and 3. These exemplary strips, fibers or wires can be composed of other materials as well, including but not limited to surgical plastic or other materials. The exemplary strips, fibers or wires 12 can be substantially straightened (or slightly-to-moderately bent as needed during steering the device through the lumen) when the chamber 10 (providing a working space) is in non-deployed position (see FIGS. 2 and 2C), and are substantially bent when actuated by a control lever 23 in the handle 20, hence, enlarging the chamber 10 and creating a larger working space inside the colon, as shown in FIGS. 2A, 2B, 2D and 3. For example, pushing or pulling the exemplary strips, fibers or strips 12 can be performed with a tube 19 that can slide in the lumen 38 by pulling and/or pushing the tube 19 proximal end lever 23 in the handle 20, as shown in FIGS. 2, 2D, 3, 9 and 9A. Further, the guide catheter 4 can be inserted inside the tube 19. The exemplary strips 12 can be covered by a soft polymer cover to avoid possible inner colon tissue damage.

According to an exemplary embodiment of the present disclosure, as shown in FIGS. 2-2D, the chamber 10 it can be deflected by pulling on the exemplary strips, fibers or wires 12, or the chamber 10 can be opened when the exemplary strips, fibers or wires 12 are pushed forward from the handle 30. In thus manner, the exemplary strips, fibers or wires 12 increase working space with in the chamber 30 to facilitate the anatomical structure to be pulled into the chamber 10 by other instruments/tools 11 being manipulated from the handle 30, as described in further details herein, and shown in, e.g., in FIG. 8.

Further, as shown in FIGS. 2B and 2D, the exemplary strips, fibers or wires 12 can be covered with a protective cover portions 70 so as to reduce damage being caused by the exemplary strips, fibers or wires 12 when they are actuated to expand the chamber 10 (i.e., which causes the exemplary strips, fibers or wires 12 to push on the surrounding tissue). As shown in FIG. 2C, the arrangement/device 1 can also include an overtube 65 which can be pushed forward toward the front of the arrangement/device 1 so as to cover the collapsed chamber 10 (e.g., to facilitate insertion and removal and containing the specimen), and pulled back to prepare for the chamber 10 for its expansion. FIG. 2D shows an illustration of the arrangement/device 1 of FIG. 2 with a scope 60 (including a camera and at least one light illuminating source) that is provided in one of the working channels 40 and facilitating a field of view 54 for positioning and propelling the exemplary arrangement/device 1.

When the instrument 1 reaches the desired position within the body, the scope 60 can be retracted inside the chamber 10, e.g., via the working channel 40 to facilitate visualization inside and/or near the chamber 10. According to another exemplary embodiment of the present disclosure, an articulating scope (which can perform similar functions as that of the scope 60) can be provided through one or more of the working channels 40 into the chamber 10. Such articulating scope can be configured to illuminate and/or provide images of the anatomical structure and tools inside and/or near the chamber 10. The articulating scope can have a distal portion that can rotate in 360 degrees and bend to provide an end part thereof so as to illuminate and visualize any portion of the anatomical structure and the tools inside and/or near the chamber 10 at any angle.

Figure 4:
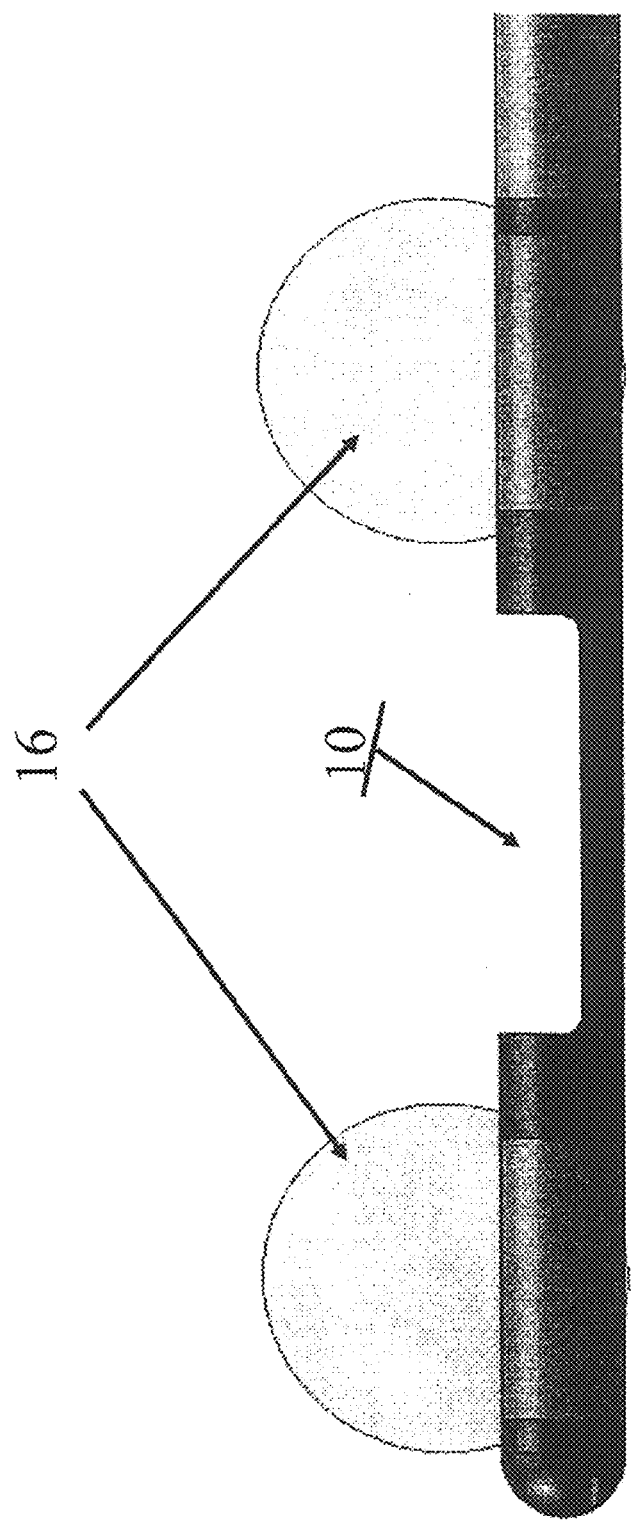
FIG. 4 is a side cross-sectional view of an exemplary embodiment of the arrangement/device according to the present disclosure which includes the chamber made from two asymmetric balloons.
Figure 5:
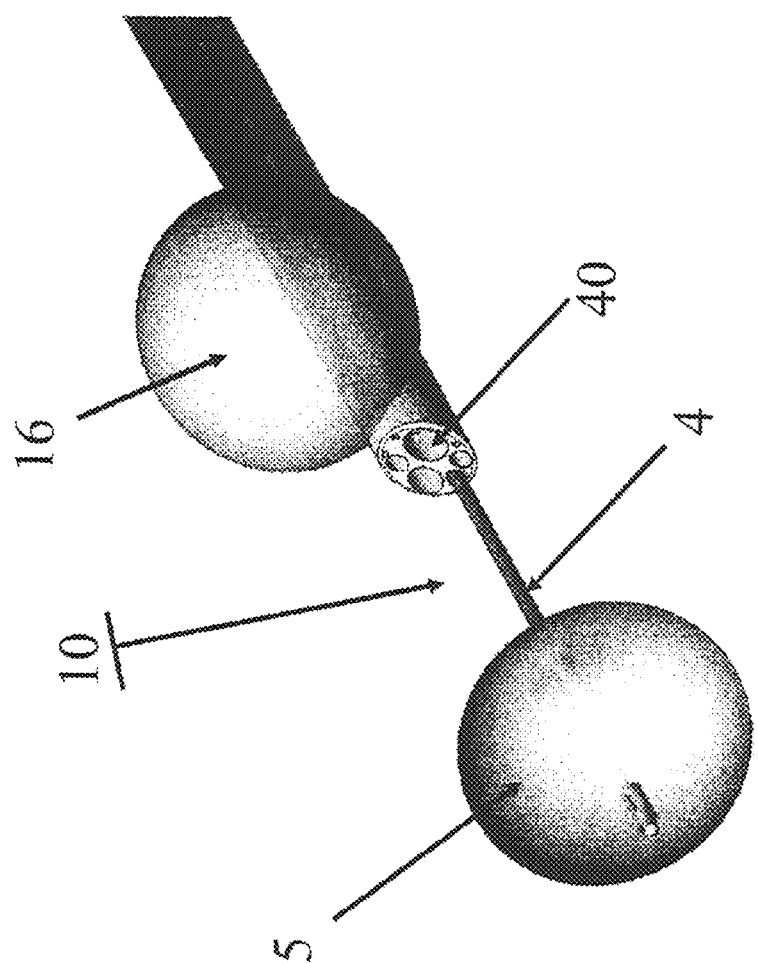
FIG. 5 is a perspective view of another exemplary of another exemplary embodiment of the arrangement/device according to the present disclosure which includes the chamber made from one asymmetric balloon together with the balloon guide catheter.
Figure 6:
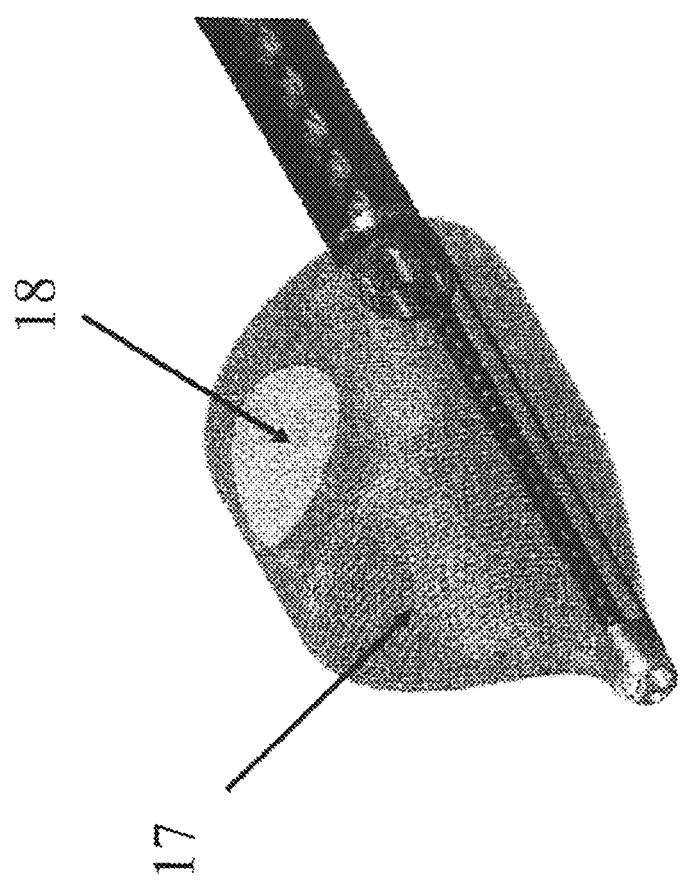
FIG. 6 is a perspective view of another exemplary of still another exemplary embodiment of the arrangement/device according to the present disclosure which includes the chamber made from metal wires braid.
Figure 7:
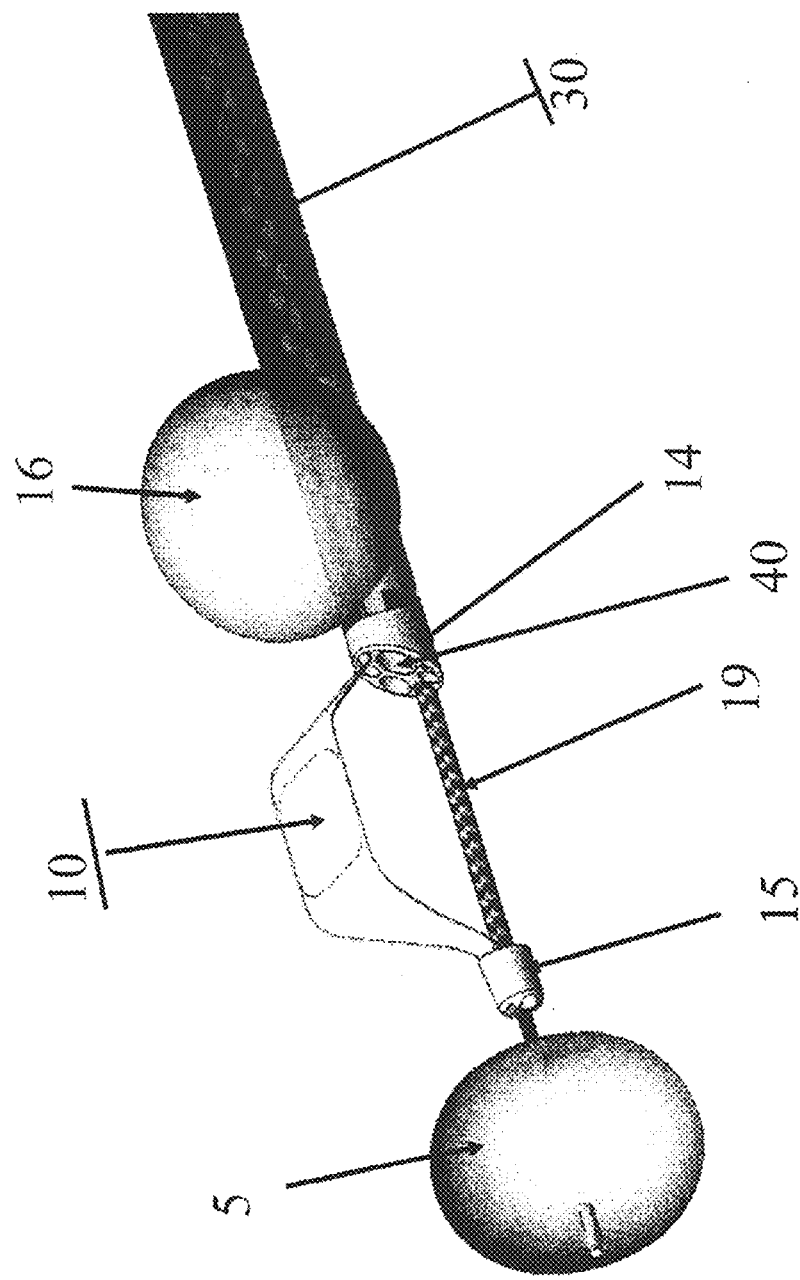
FIG. 7 is a perspective view of a further exemplary of yet another exemplary embodiment of the arrangement/device according to the present disclosure which includes the nitinol strips chamber with two blocking balloons at both sides.

In another exemplary embodiment of the present disclosure, as shown in FIG. 7, the strips 12 can be proximally connected to a first cap 14, which can be made from a solid material. The first cap 14 can have multiple holes for most or all lumens 32. The strips 12 can also be distally connected to a second cap 15 which can be smaller in diameter than the first cap 14, to facilitate a passage of large specimens, for example, polyps into the area of the chamber 10. The distal second cap 15 can include a hole for insertion of the balloon guide catheter 4. Alternatively or in addition, the exemplary chamber 10 can be made from two asymmetrical balloons 5, 16, as shown in the exemplary embodiment of FIG. 4. For example, the balloons 5, 16 can create space for the chamber 10 and the exemplary instruments/tools 11 when inflated. Alternatively or in addition, the exemplary chamber 10 can be provided using the proximal balloon 16 and the distal balloon 5, being connected to one another via their attachment to the balloon guide catheter 4, as shown in FIG. 5. Further alternatively or in addition, the exemplary chamber 10 can be provided by a braided metal wire net 17 having an opening 18 at desired location, as shown in FIG. 6.

In another exemplary embodiment of the present disclosure, at least one, and possibly two or more balloons can be used with the chamber 10 that is made from strips 12 made from a bendable material (e.g., metal). The exemplary balloon(s) 5, 16 can assist in blocking and/or isolating the chamber 10 from the rest of the colon, hence, minimizing and/or preventing the inflow and outflow of liquids and solids from and/or to the chamber 10, while the exemplary strips 12 can provide a substantially rigid and stable working space and facilitate treatment of the lesion. For example, as shown in FIG. 7, the first symmetric or asymmetric balloon 16 can be provided in proximal to the chamber 10 or the position of the strips 12. The second balloon 5 can be provided at the position that is distal to the strips 12. Alternatively, the second balloon 5 that can be connected to the guide catheter 4.

According to still another exemplary embodiment of the present disclosure, the arrangement/device 1 can include at least one camera and an illumination apparatus to provide sufficient light to the area of interest. For example, camera or cameras and illuminating component can be movable or fixed in the arrangement/device 1, for example, to the chamber 10. In one exemplary embodiment shown in FIG. 2D, the scope/front camera 50 can be used to facilitate the insertion of the arrangement/device 1 into the colon. Referring to FIG. 8, e.g., at least one, two or more additional and possibly fixed cameras 51 can be positioned so to facilitate image capture at a location of the lesion. Exemplary field views 54 of the cameras 51 can overlap, and such overlap may facilitate visualization if one or more instruments/tools blocks or adversely affects view of one of the cameras. For example, illumination can be provided by a variety of ways, e.g., by LEDs 52, 53. Exemplary front LEDs 52 can be used for the front camera 50, and in-chamber LEDs 53 can be used for the illumination in or at the chamber 10. Alternatively or in addition, a conventional flexible endoscope, having distal bendable section, can be used instead of or together with the fixed camera(s) 51 and illumination via the LEDs 52, 53.

As shown in FIGS. 9 and 9A, the exemplary arrangement/device 1 according to a further exemplary embodiment of the present disclosure can include a control handle 20 at or about its proximal end. The exemplary handle 20 can have similar shape and configuration with respect to other conventional endoscope's handles, while likely having additional channel ports and actuators than standard endoscope. For example, the ports in the handle 20 can include at least one, and possibly 2-4 or even more ports for the tool-channels 21, balloon guide catheter port 22 and particular lever 23 to control the opening and closing of the chamber 10. Additional ports can include, but not limited to, a luer port 24 for a proximal balloon inflation, and a port 26 of a vacuum catheter 25 or an irrigation catheter. The handle 20 can include switches 27, 28 for air insufflations, water irrigation and vacuum activation, as well as switch (not shown) for switching camera(s) between frontal and inner locations.

Figure 10:
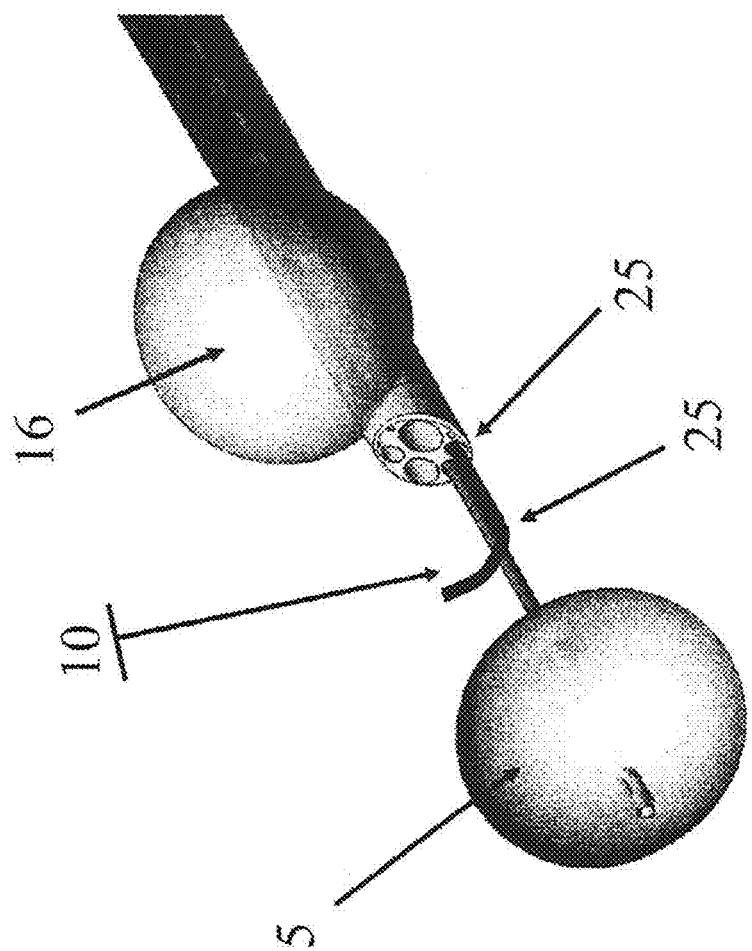
FIG. 10 is a perspective view of yet another exemplary of yet another exemplary embodiment of the arrangement/device according to the present disclosure which includes a vacuum catheter.

As illustrated in FIG. 10, the exemplary arrangement/device 1 according to a still further exemplary embodiment of the present disclosure can include a vacuum catheter with a bent tip 25, inserted in a vacuum lumen 36 through a vacuum port 26. The vacuum catheter can operate as a standalone (as describe herein), and/or may be inserted into tool channel 40 and deflect. Further, the vacuum catheter can be manipulated to reach all or most areas inside and around the chamber 10, hence, providing an access for elimination of liquids and solids from and around the chamber 10. In another exemplary embodiment of the present disclosure, the chamber 10 can include bendable and steerable section, which can be actuated at the lever 23, which when pulled, the instrument 1 is articulated, and when pushed, the chamber 10 is opened (or increased in size). Thus, movements of the exemplary arrangement/device 1 in the colon can be facilitated. According to a further exemplary embodiment, a locking mechanism can be provided which can, e.g., rotate one or more times (e.g., counterclockwise or counter-clockwise) to lock the lever 23.

Figure 11:
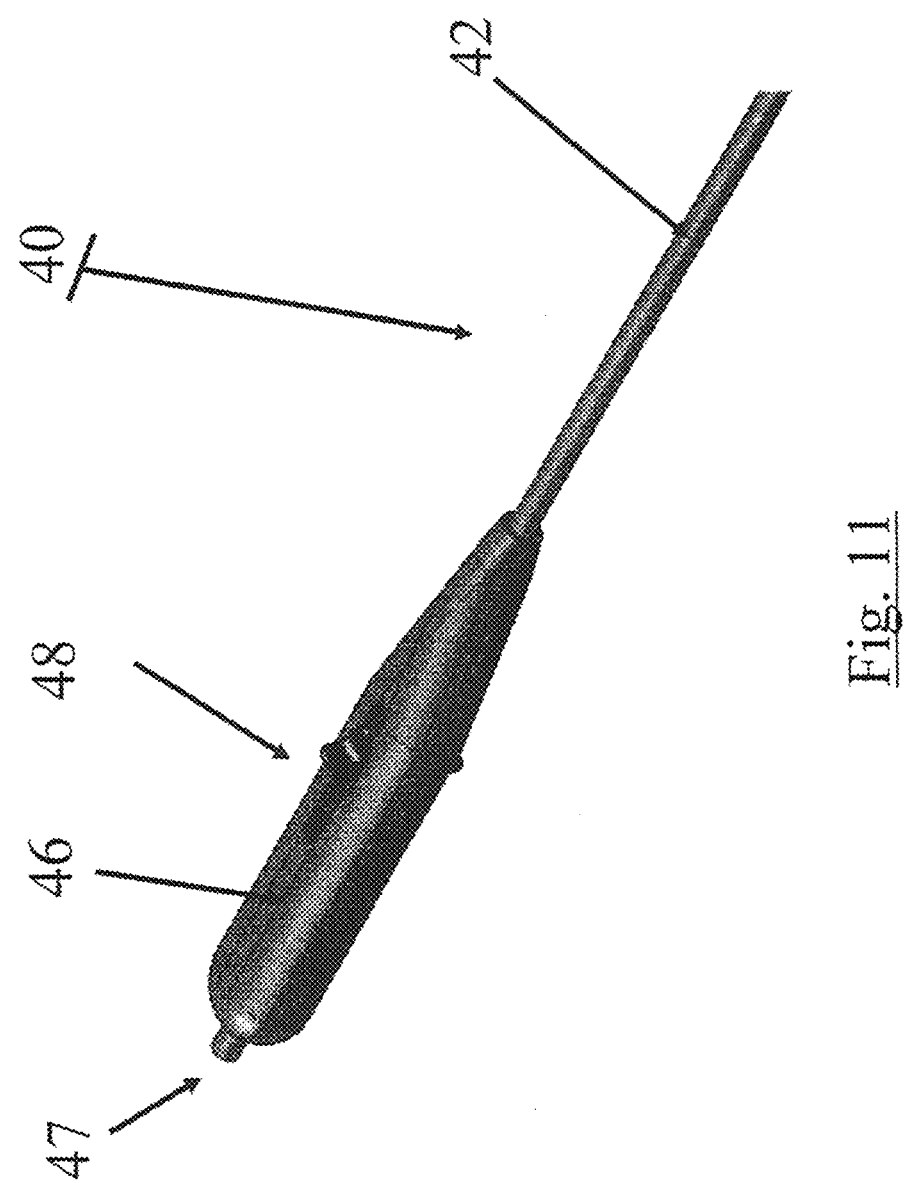
FIG. 11 is a perspective view of yet another exemplary of another exemplary embodiment of the arrangement/device according to the present disclosure which includes a tool-channel.

According to still another exemplary embodiment of the present disclosure, the exemplary arrangement/device 1 can include the instruments/tools 11 and/or tool-channels 40, as shown in FIG. 11. When the exemplary instruments/tools 11 are inserted in the tool channels 40, distal ends 41 thereof change the position(s) and/or shapes of the instruments/tools 11, for example, rotated, axially moved, bent at desired angles, whenever the position and shape of the associated tools channels 40 are changed, as shown in FIGS. 12 and 12A (compare to FIG. 12B). The tool channels 40 can be actuated and manipulated at or about proximal end of the exemplary arrangement/device of the present disclosure. The described maneuverability of the tool-channels 40, for example, their distal ends 41 provide and/or facilitate multidirectional and multiangular approach to the target lesion.

For example, the tool-channels 40 can include at least one, and preferably two, three or more lumen tubes 42, which can be made of polymer, possibly having high torque-ability, low friction, connected at or about their distal ends to an additional section 41, which can have "elevators" 43. The exemplary polymer tube(s) 42 can be reinforced with other materials to change its/their structural or/and functional properties. The elevator 43 can be a flexible bendable section, made, e.g., from a laser cut nitinol tube 44, and/or actuated, e.g., bent, using one or two metal wires 45. The instruments/tools 11 can be inserted in the first (e.g., relatively large) lumen of the tube 42, and the wire 45 can be inserted in the second (e.g., relatively small) lumen of the tube 42.

As shown in FIG. 13, the ability of the tool-channel tubes 42 to move, independently or simultaneously, axially (e.g., pushing, pulling directions), rotate and bend using the elevator 43, facilitates the instruments/tools 11 or/and the tool-channels 40 in reaching any point within and around the chamber 10, and can provide possibly an unlimited range of instrumental freedom within the working space. For example, as shown in FIG. 11, the tool channel 40 can include one or more handles 46 connected to the tube 42 at or about a proximal side of the tube 42, and can be used for a manipulation of the elevator 43, and utilize a port 47 for an insertion of the exemplary instrument/tool. 11. The exemplary tool-channel handle 46 can include a slider or knob 48 which can be used to actuate, e.g., pull and release a wire 45, as shown in FIG. 12. Any standard tool(s) can be used with the exemplary tool-channel(s) 40. Alternatively or in addition, articulating tools having maneuverable distal ends, e.g., with at least two degrees of freedom, can be used.

According to yet a further exemplary embodiment of the present disclosure, a method for implementing the exemplary arrangement/device 1 according to the present disclosure can be provided. Such exemplary method can be utilized as follows:

i. Perform a standard colonoscopy and identifying a lesion that may not be treated using standard endoscopy and techniques.

ii. Insert a balloon guide catheter, inflating the balloon and removing the standard colonoscope (the balloon catheter and inflated balloon are left in place). The balloon guide catheter can be used as a guide-wire to facilitate the insertion of the exemplary arrangement/device 1.

iii. Insert the exemplary arrangement/device 1 over the balloon guide catheter, until the chamber is in the proximity to the lesion.

iv. Deploy and adjust the chamber 10 of the exemplary arrangement/device 1 to preferred dimensions. Readjust the chamber 10 during the procedure as needed.

v. Clean an operative area with a provided suction catheter. If desired, inflate a proximal balloon, a distal balloon or both proximal and distal balloons for the treatment area isolation.

vi. Insert the tool-channels.

vii. Insert the instruments/tools into the tool-channels. Manipulate the tool-channels to optimize and facilitate the instruments/tools approach to the lesion.

viii. Perform a procedure, e.g., closing a colonic perforation, removing a large colon polyp or tumor, stopping a bleeding, closing diverticuli, removing an appendix, treating other body luminal lesions.

The foregoing merely illustrates the principles of the present disclosure. Various modifications and alterations to the described embodiments will be apparent to those skilled in the art in view of the teachings herein. For example, more than one of the described exemplary arrangements, radiations and/or systems can be implemented to implement the exemplary embodiments of the present disclosure. It will thus be appreciated that those skilled in the art will be able to devise numerous systems, arrangements and methods which, although not explicitly shown or described herein, embody the principles of the present disclosure and are thus within the spirit and scope of the present disclosure. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An endoscopic surgical system for accessing a target tissue structure comprising;
   an endoscopic device having a handle at a first portion, a longitudinal axis, a chamber at a second portion and first and second lumens extending through the device, the chamber having a proximal end portion and a distal end portion, each of the lumens having an opening to the proximal end portion of the chamber for access to the proximal end portion of the chamber, the chamber movable from a first collapsed position for insertion to an expanded position to increase a working space adjacent the target tissue structure;
   a first tube having a distal tip and movable within the first lumen to orient a first instrument through the first tube and into the chamber, the first tube controllable at the proximal end for movement within the first lumen, the proximal end portion of the chamber configured to allow for passage of a distal portion of the first tube;
   a second tube having a distal tip and movable within the second lumen to orient a second instrument through the second tube and into the chamber, the second tube controllable at a proximal end for movement within the second lumen, the proximal portion of the chamber configured to allow for passage of a distal portion of the second tube; and
   the first and second tubes movable to orient the first and second instruments to achieve triangulation within the increased working space formed by the chamber;
   the chamber expandable to increase the working space adjacent the target tissue structure by moving the target tissue structure laterally with respect to the longitudinal axis of the device such that a distance between the distal tip of the first and second tubes and the target tissue structure within the increased working space is increased such that first and second instruments inserted through the respective first and second tubes have an increased space to maneuver within the chamber and to act on the target tissue structure within the increased working space formed by the chamber.

2. The endoscopic device of claim 1, wherein the chamber comprises a plurality of members movable between collapsed and expanded positions.

3. The endoscopic device of claim 2, further comprising a cover positioned over the plurality of members of the chamber to protect the body lumen during insertion.

4. An endoscopic device of claim 2, wherein a transverse arc intersecting all of the plurality of members of the chamber extends around less than full circumference of a circle.

5. The endoscopic device of claim 2, wherein the plurality of members are connected at a proximal end to a cap.

6. The endoscopic device of claim 2, wherein the plurality of members are connected at a distal end to a cap.

7. The endoscopic surgical system of claim 2, wherein the members are covered with a protective cover portion.

8. The endoscopic device of claim 1, wherein the chamber is movable in a lateral direction to only one side of a longitudinal axis of the device.

9. The endoscopic surgical system of claim 1, wherein the endoscopic device has a third lumen, and further comprising an endoscope receivable with the third lumen for visualizing the tissue structure within the chamber.

10. The endoscopic surgical system of claim 9, wherein the endoscope is an articulating endoscope such that a tip of the endoscope is movable laterally within the chamber.

11. The endoscopic surgical system of claim 1, wherein the first and second tubes are movable axially from a position wherein distal tips are outside the chamber to a position wherein the distal tips are inside the chamber, and the distal tips bendable within the increased working space formed by the chamber to provide angular access to the target tissue structure thereby enabling triangulation for performance of a surgical procedure on the target tissue structure.

12. The endoscopic surgical system of claim 1, wherein the chamber is expanded within a colon of a patient.

13. The endoscopic surgical system of claim 1, wherein the first and second tubes are independently manipulable from the proximal end.

14. The endoscopic surgical system of claim 1, wherein the chamber includes a side opening for the target tissue structure.

15. The endoscopic surgical system of claim 14, wherein the chamber includes flexible elements and the side opening is between the flexible elements.

16. The endoscopic surgical system of claim 1, wherein the chamber is adjustable to provide the working space with multiple sizes.

17. The endoscopic surgical system of claim 1, wherein the chamber in the expanded position is non-cylindrically shaped and asymmetrical.

18. The endoscopic surgical system of claim 1, wherein the chamber has a partially rigid portion.

19. The endoscopic surgical system of claim 1, wherein the first and second tubes are bendable at a distal end by a wire.

20. The endoscopic surgical system of claim 1, wherein the endosopic device has first and second working ports and the first tube is inserted through the first working port and the second tube is inserted through the second working port.

21. The endoscopic surgical system of claim 1, wherein the chamber includes a plurality of strips of metal.

* * * * *